United States Patent [19]
Kosasky

[11] Patent Number: 6,149,604
[45] Date of Patent: Nov. 21, 2000

[54] INSTRUMENT FOR MEASURING SALIVA VISCOELASTICITY TO DETERMINE FEMALE FERTILE PERIOD

[76] Inventor: Harold J. Kosasky, 25 Boylston St., Chestnut Hill, Mass. 02167

[21] Appl. No.: 09/218,830

[22] Filed: Dec. 22, 1998

Related U.S. Application Data

[63] Continuation-in-part of application No. 09/012,476, Jan. 23, 1998, Pat. No. 5,851,190, which is a continuation-in-part of application No. 08/589,138, Jan. 19, 1996, abandoned, which is a continuation-in-part of application No. 08/524,741, Sep. 7, 1995, Pat. No. 5,640,968.

[51] Int. Cl.$^7$ .................................................. A61B 10/00
[52] U.S. Cl. .......................................... 600/551; 600/573
[58] Field of Search ................................. 600/551, 573, 600/580, 300; 73/54.19, 54.22

[56] References Cited

U.S. PATENT DOCUMENTS

| | | |
|---|---|---|
| 3,982,423 | 9/1976 | Schuster . |
| 4,072,045 | 2/1978 | Kopito . |
| 4,167,110 | 9/1979 | Kopito et al. . |
| 4,237,725 | 12/1980 | Kopito et al. . |
| 4,628,941 | 12/1986 | Kosasky . |

OTHER PUBLICATIONS

Gerald Oster et al., "Cyclic Variation of Sialic Acid Content in Saliva," American Journal of Obstetrics and Gynocology, vol. 114, No. 2, pp. 190–193 (Sep. 15, 1972).

L.E. Kopito et al., "The Tackiness Rheometer Determination of the Viscoelasticity of Cervical Mucus," Human Ovulation, Elsevier North–Holland Biomedical Press, 1979, pp. 351–361.

*Primary Examiner*—Dinh X. Nguyen
*Attorney, Agent, or Firm*—Morse, Altman & Martin

[57] ABSTRACT

An instrument for measuring saliva viscoelasticity to determine a woman's fertile period comprised of a sheath, a cap, and an escapement. The includes a barrel with a pair of elongated slots, a piston within the barrel with protrusion that extend into and beyond the slots, and a sleeve over the barrel with a pair of spiral groove into which the protrusions fit. As the sleeve rotates about the barrel, the grooves spiral up or down, causing the piston to move axially within the barrel. A central cavity within the barrel includes a constricted throat near the top end. The escapement is a U-shaped strip of plastic that fits into the cavity and attaches at its cross portion to the piston. The ends of the escapement arms have mating surfaces that are roughened so that the saliva sample will fracture before it separates from the surfaces. As the escapement is pulled into the cavity, the throat operates to press the mating surfaces together. After the throat is passed, the escapement cross portion acts as a spring to pull the mating surfaces apart against the viscoelasticity of the saliva. The amount of time it takes for the saliva to fracture under pressure from the spring is measured, adjusted based on the temperature of the saliva, and used to indicate whether the user is in her fertile period or not.

17 Claims, 12 Drawing Sheets

INSTRUMENT FOR MEASURING SALIVA VISCOELASTICITY TO DETERMINE FEMALE FERTILE PERIOD

RELATED APPLICATION

This application is a continuation-in-part of pending application Ser. No. 09/012,476, now U.S. Pat. No. 5,851,190, entitled INSTRUMENT FOR MEASURING SALIVA VISCOELASTICITY TO DETERMINE FEMALE FERTILE PERIOD, filed on Jan. 23, 1998, which is a continuation-in-part of application Ser. No. 08/589,138, entitled INSTRUMENT FOR MEASURING SALIVA VISCOELASTICITY TO DETERMINE FEMALE FERTILE PERIOD, filed on Jan. 19, 1996, now abandoned, which is a continuation-in-part of application Ser. No. 08/524,741, now U.S. Pat. No. 5,640,968, entitled INSTRUMENT FOR MEASURING SALIVA VISCOELASTICITY TO DETERMINE FEMALE OVULATION TIME, filed on Sep. 7, 1995.

GOVERNMENT FUNDING

The research involved in this application was funded in part by the National Institutes for Health, grant number 1 R41 HD32218-01. The intellectual property rights of the applicant and the government of the United States of America are governed by Title 37 Code of Federal Regulations Part 401.

BACKGROUND OF THE INVENTION

1. Field of the Invention

The present invention relates to the measurement of the viscoelasticity of saliva, and more particularly, to a device for the measurement of saliva viscoelasticity in order to determine a woman's fertile period.

2. The Prior Art

It has been known that the cervical mucus of a female has a maximum fluidity just before ovulation, where ovulation is defined as the moment that an ovum is released from the follicle. This knowledge lead to the applicant's previous activities in the development of techniques for monitoring the viscoelasticity, or tackiness, and other properties of cervical mucus as a predictor of time of ovulation and to improvements in rheometer or viscometer apparatus for measuring such viscoelastic properties. See, for example, L. E. Kopito and H. J. Kosasky, "The Tackiness Rheometer Determination of the Viscoelasticity of Cervical Mucus," *Human Ovulation*, edited by E. S. E. Hafez, Elsevier, North-Holland Biomedical Press, 1979, pp. 351 et seq., and U.S. Pat. Nos. 4,002,056 and 4,167,110. Though the viscoelasticity of the cervical mucus has several small dips in its characteristic curve of viscosity versus time preceding, during, and following ovulation (a four-day period), there is a distinct identifiable minimum viscoelasticity. Instruments designed to measure this effect are described in, for example, U.S. Pat. Nos. 4,002,056 and 4,072,045.

Saliva is now known to undergo physiochemical changes during the menstrual cycle, including a change in its viscoelasticity. Especially pronounced is the change in viscoelasticity of sublingual saliva, the saliva found under the tongue. See, for example, S. S. Davis, "Saliva is Viscoelastic", Experientia, 26:1298, (1970), and R. H. Davis et al., "Saliva Viscosity Reflects the Time of Ovulation", Experientia, 30:911, (1974). As described in U.S. Pat. No. 4,779,627, issued on Oct. 25, 1988, to the present applicant, and entitled PROCESS AND APPARATUS FOR DETERMINING FEMALE OVULATION TIME BY MEASUREMENT OF SALIVA VISCOELASTICITY, the applicant previously discovered that sublingual saliva has a unique and reliably measurable minimum in viscoelasticity that is coincident with the ovulation cycle and its surge of estradiol.

There are devices on the market for measuring viscoelasticity to determine ovulation time, but these devices are designed to use cervical mucus as a sample medium, rather than saliva. The viscoelasticity of cervical mucus is an order of magnitude higher than that of saliva. Consequently, devices designed to use cervical mucus as a sample medium are typically not sensitive enough to use saliva as a sample.

The above-identified U.S. Pat. No. 4,779,627, in addition to disclosing a process for determining female ovulation time by measuring saliva viscoelasticity, discloses a device for measuring the viscoelasticity of the sublingual saliva. The device has a shape somewhat like a syringe, with an outer cup, an inner cup concentric with and located within the outer cup, and a plunger. A roughened surface on the end of the plunger holds the saliva sample. The plunger is inserted into the inner cup until the saliva sample is compressed against the bottom of the inner cup. A predetermined amount of weight pulls the inner cup downward, stretching the saliva sample. If the viscoelasticity of the saliva is low, the saliva sample will fracture, causing the inner cup to fall to the bottom of the outer cup. An indicator at the bottom of the outer cup indicates that the inner cup has fallen to the bottom which, in turn, indicates that ovulation will soon take place. If, however, the viscoelasticity of the saliva is high, the saliva sample will hold the plunger and inner cup together so that the inner cup will not fall to the bottom, indicating that ovulation will not take place in the near future.

This device has several disadvantages. The first disadvantage is that the device can only be used conveniently for one person. The amount of weight that pulls the inner cup downward is selected for a specific person. There must have been a sublingual saliva sample measured from the same person at a time when the sublingual saliva is known to have the minimum viscoelasticity in order to select the amount of weight.

The second disadvantage is that the device must be taken apart in order to take a sample. The plunger must be removed from the inner cup before being inserted in the mouth to obtain a saliva sample. This has the potential for the person to easily contaminate the saliva sample by incorrectly reinserting the plunger after taking the sample, invalidating the measurement.

SUMMARY OF THE INVENTION

One object of the instrument of the present invention is to provide an instrument for measuring saliva viscoelasticity to determine a woman's fertile period that is easy and convenient to use.

Another object is to overcome the need to calibrate the instrument to an individual.

A further object of the present invention is to reduce the possibility of contamination of the saliva sample prior to measurement.

The instrument of the present invention for measuring saliva viscoelasticity to determine a woman's fertile period is comprised of a sheath, a cap, and an escapement. The sheath includes a barrel, a piston, and a sleeve. The barrel is a hollow cylinder with a pair of elongated, opposed slots. The piston resides within the barrel and has a pair of protrusions that extend into and beyond the slots. The sleeve fits over the barrel and rotates about the barrel. The inside surface of the sleeve includes a pair of spiral grooves in which the piston protrusions fit, so that, as the sleeve rotates, the grooves spiral up or down, causing the piston to move axially within the barrel. Alternatively, the protrusions are replaced by ball bearings for a more smooth piston motion. The cap fits over the top end of the sheath in order to protect the inner components of the instrument.

The barrel includes a central cavity that is rectangular at the top end. The cavity extends into the sheath, initially decreasing in width and then increasing in width, to form a constricted throat. The rectangular cavity eventually opens into a circular cavity, the space in which the piston moves.

The escapement fits in the rectangular cavity and attaches to the piston, preferably by a removable connector. The escapement is an elongated U-shaped strip of plastic or composite that is either composed of or coated with an electrically-conductive material. Attached to or molded into the upper ends of the arms are a pair of opposed plates that have mating surfaces. The arms also include a pair of opposed elbows. The cross portion forms a spring that forces the mating surfaces away from each other.

In operation, the piston is initially at the top of the circular portion of the cavity, and the escapement is attached to it and in the rectangular portion of the cavity. The mating surfaces are outside of the cavity. The user dips the mating surfaces into the saliva pool under her tongue. The surfaces are roughened so that the saliva will fracture before it separates from the surfaces. After the saliva sample is taken, the user rotates the sleeve to pull the escapement into the cavity. As the elbows pass through the throat, the mating surfaces are pressed together, compressing the saliva sample. As the elbows pass out to the throat, the spring applies a force to pull the mating surfaces apart. At the same time, the elbows close a start switch on a timer circuit, the components of which are located either internal or external to the sheath. As the escapement continues downward movement to the bottom of the cavity, the mating surfaces remain held together by the viscoelasticity of the saliva. Eventually, the force of the spring overcomes the viscoelasticity of the saliva and the mating surfaces separate. When that happens, the elbows close a stop switch on the timer. The separation time measured by the timer is adjusted depending upon the saliva temperature at the time of the measurement, and the result of that calculation is indicated on a pair of light-emitting diodes or a liquid crystal display.

Other objects of the present invention will in part be obvious and will in part appear hereinafter.

BRIEF DESCRIPTION OF THE DRAWINGS

For a fuller understanding of the nature and object of the present invention, reference is made to the accompanying drawings, wherein.

DETAILED DESCRIPTION

The Instrument

The preferred embodiment 10 of the invention is shown in FIGS. 1–5. It is comprised of three basic components: a sheath 12, a cap 14, and an escapement 20.

Figure 1:
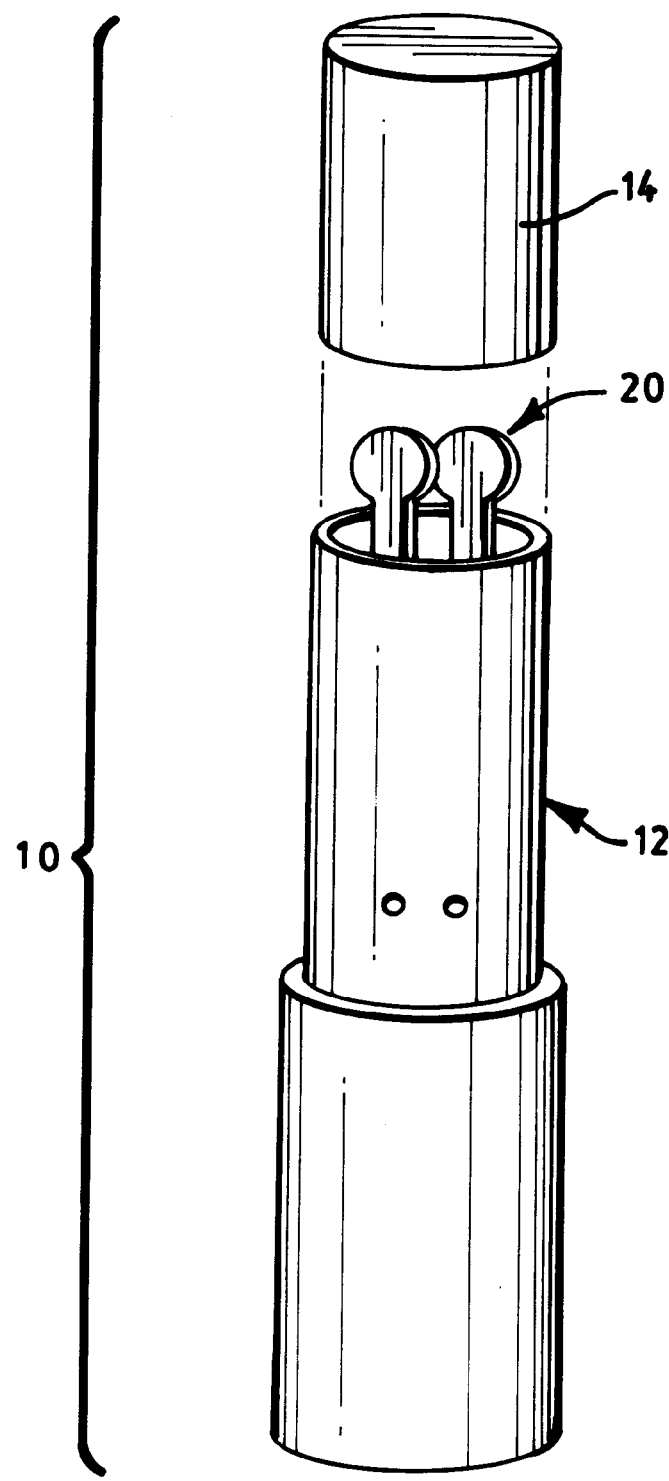
FIG. 1 is a perspective view of the instrument of the present invention.
Figure 2:
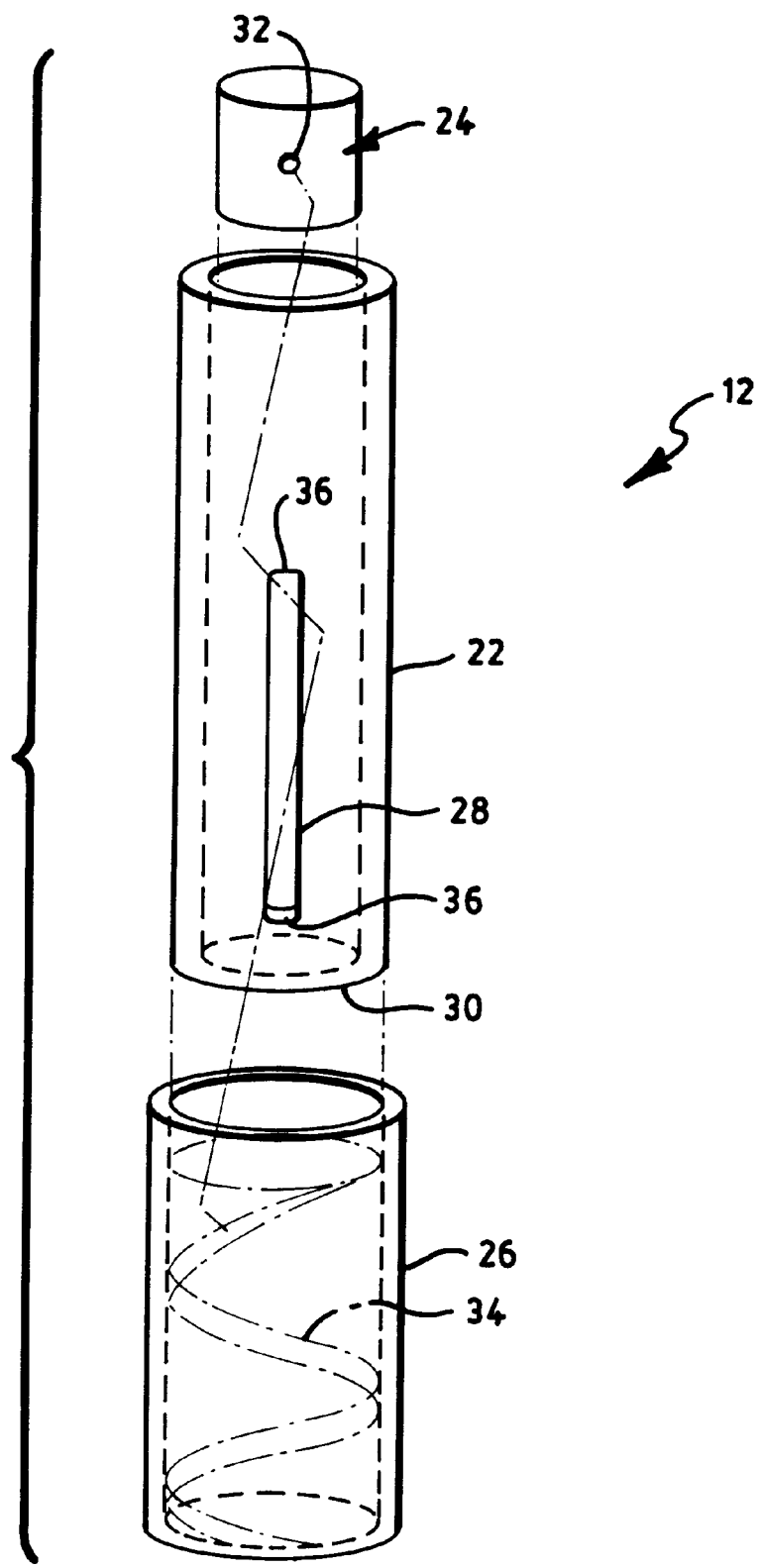
FIG. 2 is an exploded, partial phantom view of the sheath of FIG. 1.
Figure 4:
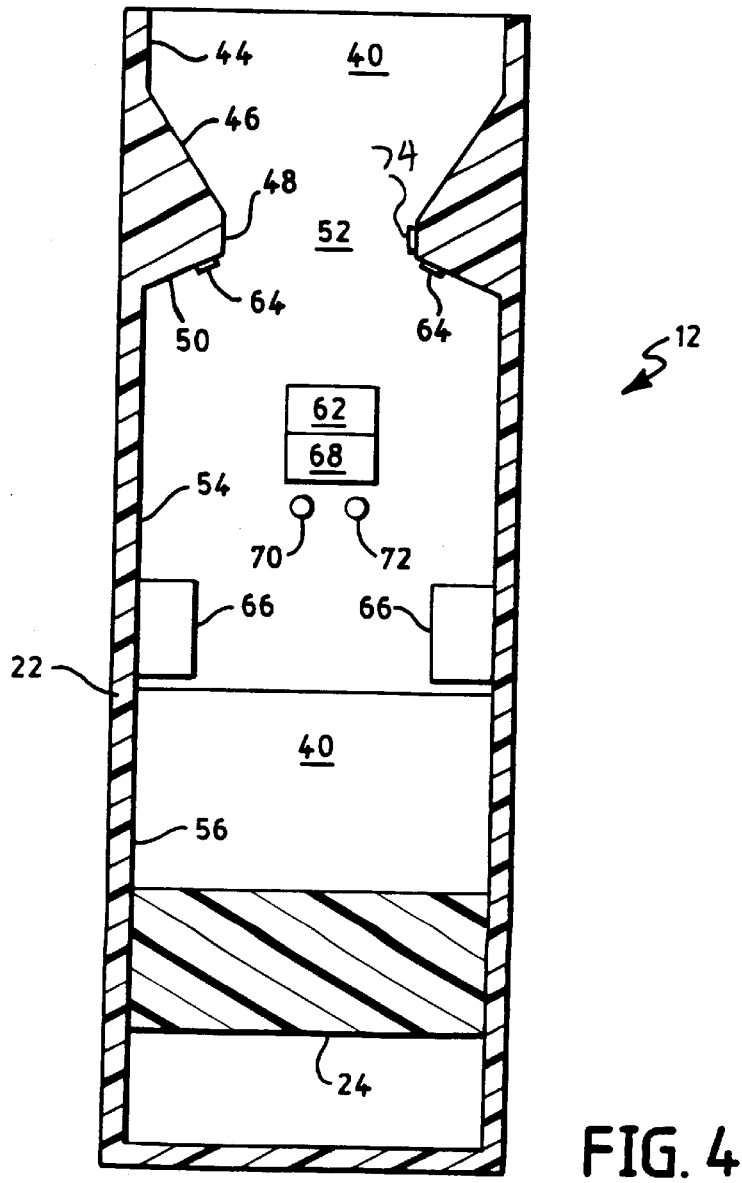
FIG. 4 is a side cross-sectional view of the sheath.

FIGS. 2 and 4 show an exploded and cross-sectional view of the sheath 12. It includes three components: a barrel 22, a piston 24, and a sleeve 26. The barrel 22 is a hollow cylinder with a pair of opposed slots 28 near or at the bottom end 30 (only one slot is shown in the figures). The slots 28 are elongated parallel to the axis of the barrel 22. The piston 24 is also a cylinder that fits within the barrel 22. The piston 24 has an outside diameter slightly smaller than the inside diameter of the barrel 22 so that the piston 24 fits snuggly within the barrel 22, but also can reciprocate within the barrel 22. The outer surface of the piston 24 includes a pair of opposed protrusions 32 (only one is shown) that slide within the slots 28 as the piston 24 reciprocates. The protrusions 32 extend beyond the outer surface of the barrel 22. The sleeve 26 is also cylindrical and fits over the barrel 22. The inside diameter of the sleeve 26 is slightly larger than the outside diameter of the barrel 22 so that the sleeve 26 can rotate about the barrel 22. The inside surface of the sleeve 26 includes a pair of interlaced spiral grooves 34 (only one of which is shown). The protrusions 32 reside within these grooves 34 so that, as the sleeve 26 rotates, the grooves 34 spiral up or down, depending upon the direction of rotation. Because the protrusions 32 are limited to axial motion within the slots 28, the piston 24 is pushed axially within the barrel 22. The range of the piston's motion is limited by the length of the slots 28, where the protrusions 32 make contact with the slot ends 36 and cannot move any farther.

In an alternative embodiment, and in order to provide a smoother motion for the piston, each protrusion 32 is replaced by a depression and a ball bearing. The ball bearing sits in the depression and rides within the spiral groove as the sleeve turns.

Figure 3:
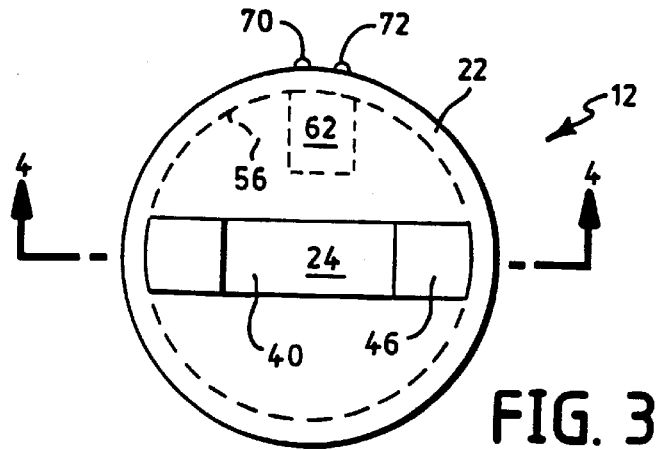
FIG. 3 is a top view of the sheath.

The central cavity 40 of the sheath, when viewed from the open end of the sheath 12, as in FIG. 3, is rectangular in shape and the rectangle is centered about the axis of the sheath 12. The narrow dimension of the cavity 40 is the slightly larger than the width of the escapement 20, as described below. The cavity 40 extends into the sheath 12 a short distance, as at 44. Extending further into the sheath 12, the cavity 40 decreases in size, as at 46, remains substantially constant, as at 48, for a short distance, and then increases, as at 50. The narrowing and widening of the cavity 40 defines a throat 52. The cavity 40 continues with a rectangular shape for a distance, as at 54, until it enlarges to a cylindrical shape in which the piston 24 operates, as at 56.

Figure 5:
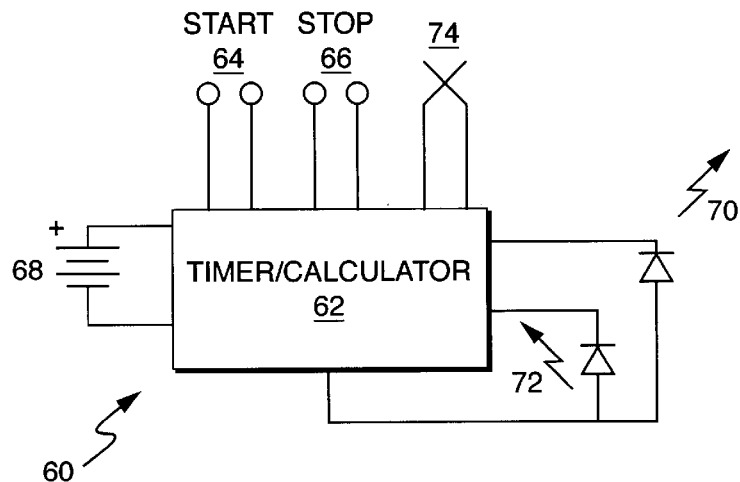
FIG. 5 is an electrical schematic of the timing circuit.

Within the sheath 12 is an electronic circuit 60, a schematic diagram of which is shown in FIG. 5. The circuit 60 is composed of a timer/calculator 62, a pair of start panels 64, a pair of stop panels 66, a temperature sensor 74, a battery 68, and the two light-emitting diodes (LED's) 70, 72. The LED's 70, 72 are mounted within the wall of the sheath 12 so that they are visible by the user. When the start panels 64 are electrically connected together, as described below, the timer/calculator 62 begins timing. When the stop panels 66 are electrically connected together, as described below, the timer/calculator 62 stops timing. The timer/calculator 62 then reads the temperature sensor 74 to determine the temperature of the saliva and adjusts the elapsed time accordingly, as described below. Finally, the timer/calculator 62 compares the adjusted elapsed time to a predetermined value, and if the adjusted elapsed time is greater, it momentarily energizes one of the LED's 70, otherwise it momentarily energizes the other LED 72. The battery 68 supplies electrical power to the timing circuit 60.

The temperature sensor 74 is shown is being on the wall 48 of the throat 52. The ideal location for the temperature sensor is on the plates 100 of the escapement 20, since the purpose of the temperature sensor 74 is to measure the temperature of the saliva, and the saliva is located on the plates 100. However, it is extremely impractical to locate the temperature sensor 74 on the plates 10, since it would require at least a two-wire electrical connection and a temperature sensor on the escapement 20. The escapement 20 is intended to be a one-use, throw-away item, and the inclusion of the temperature sensor would make the escapement too expensive. The preferred location of the throat wall 48 for the temperature sensor 74 is a compromise. The escapement 20 is in contact with the throat wall 48 for a significant period of time, long enough to get an adequate reading of the escapement temperature. It is assumed that the difference between the temperatures of the saliva and the escapement 20 is relatively insignificant. The present invention contemplates that the temperature sensor 74 may be located where ever it is capable of determining the temperature of the saliva. For example, a temperature sensor that is capable of measuring the temperature of the saliva without physical contact may be located away from the throat 52.

Alternatively, various combinations of the timer/calculator 62, battery 68, and LED's 70, 72 are mounted on the outside of the sheath 12. Alternatively, the timer/calculator includes a microprocessor for controlling the timer and adjustment operations and a liquid-crystal display (LCD), rather than a pair of LED's, for displaying the results. The LCD would typically display the adjusted elapsed time.

The cap 14 is shaped substantially like an inverted cup and is composed of a rigid plastic. It fits over the top end of the sheath 12 in order to protect the inner components of the instrument 10. It can be retained in any manner that is appropriate, such as by mating threads or friction fit.

Figure 6:
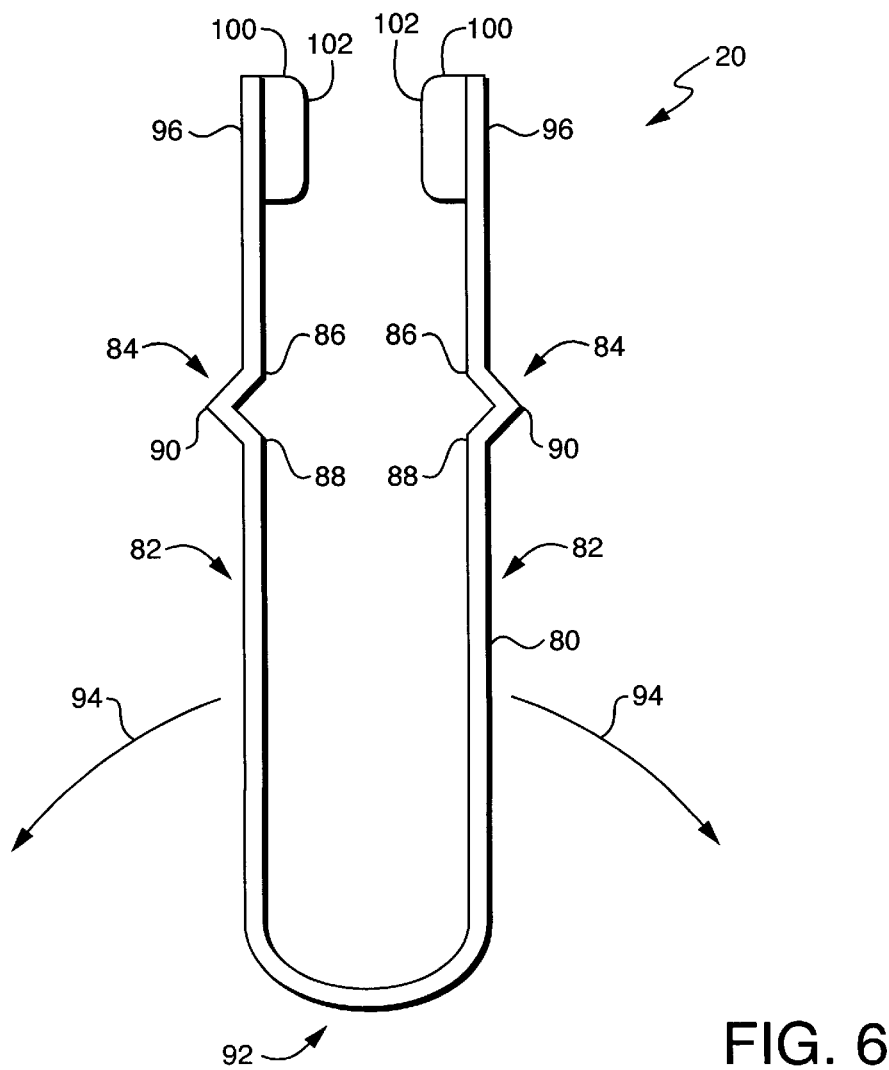
FIG. 6 is a side view of the escapement of FIG. 1.

As shown in FIG. 6, the escapement 20 is a substantially elongated U-shaped strip of plastic or composite 80 that is coated with an electrically-conductive material. In an alternate configuration, the strip 80 is an electrically-conductive plastic or composite. The strip 80 is wide enough to prevent the arms 82 from twisting longitudinally within the cavity 40 in normal use. The arms 82 include a pair of opposed elbows 84, which are created by three bends in the strip 80. The upper bend 86 and the lower bend 88 angle approximately 45° outwardly from the plane of the arm 82, forming the center bend 90 of approximately 90°.

The cross portion of the escapement 20 is at the inner extremities of the arms 82. The curve of the cross portion forms a spring 92, which forces the arms 82 to pivot outwardly from a vertical position to a horizontal position, as at 94. The amount of force exerted by the spring 92 is dependent on the material of which the strip 80 is composed and the thickness of the strip 80. The preferred force is described below.

In one embodiment of the escapement 20, at the outer extremity of each arm 80 is a frame 96 into which are permanently mounted plates 100 by a substantially waterproof adhesive. In a second embodiment, the plates 100 are removably mounted so that the plates 100 may be discarded and replaced. In a third embodiment, the plates 100 are integrally formed with the arms 80. The plates 100 have mating surfaces 102, which are detailed below.

In the preferred embodiment, the escapement 20 is removable so that it can be replaced after each use. To facilitate removal and replacement, there is a connector 104 between the escapement 20 and the piston 24. In one embodiment, shown in FIG. 7, the connector 104 is in the form of a snap, such as found on clothing, where the male component 106 is adhered to or molded into the spring 92 of the escapement 20 and the female component 108 is attached to the piston 24. In another embodiment, shown in FIG. 8, the piston 24 includes a pair of tongues 112 that curve up from the piston upper surface 114. The tongues 112 are weak enough so that when the escapement 20 is pushed down onto them, they deflect downwardly. As the spring 92 of the escapement 20 makes contact with the piston 24, the tongues 112 snap back into normal position, holding the escapement between the tongues 112 and the piston 24. The escapement 20 is removed by pulling it hard enough to bend the tongues 112 upwardly away from the piston surface 114.

Figure 9:
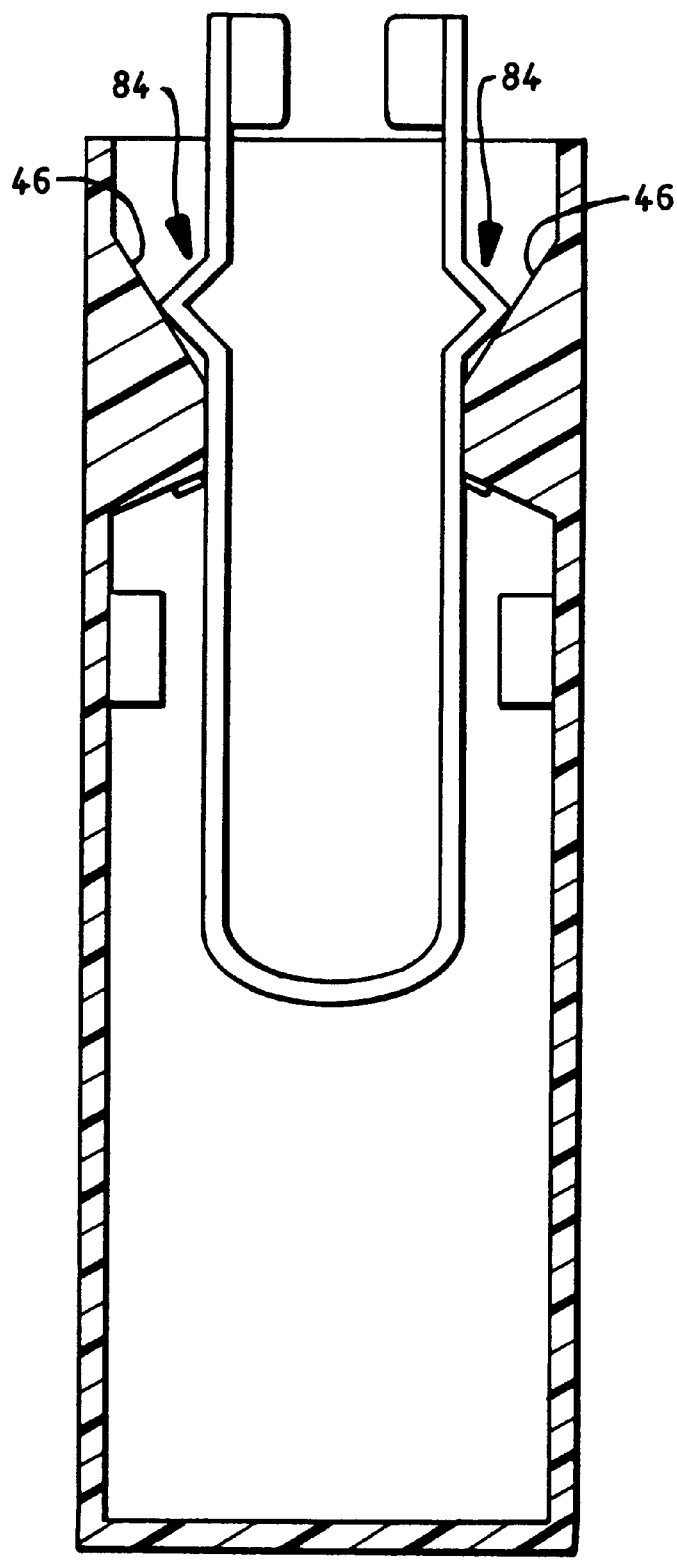
FIG. 9 is a cross-sectional view of the first step of operation.

FIGS. 9–12 detail, in cross-section, the internal operation of the instrument 10. FIG. 9 shows the initial position of the piston 24 and escapement 20, which is at the upper limit of the piston 24.

Figure 10:
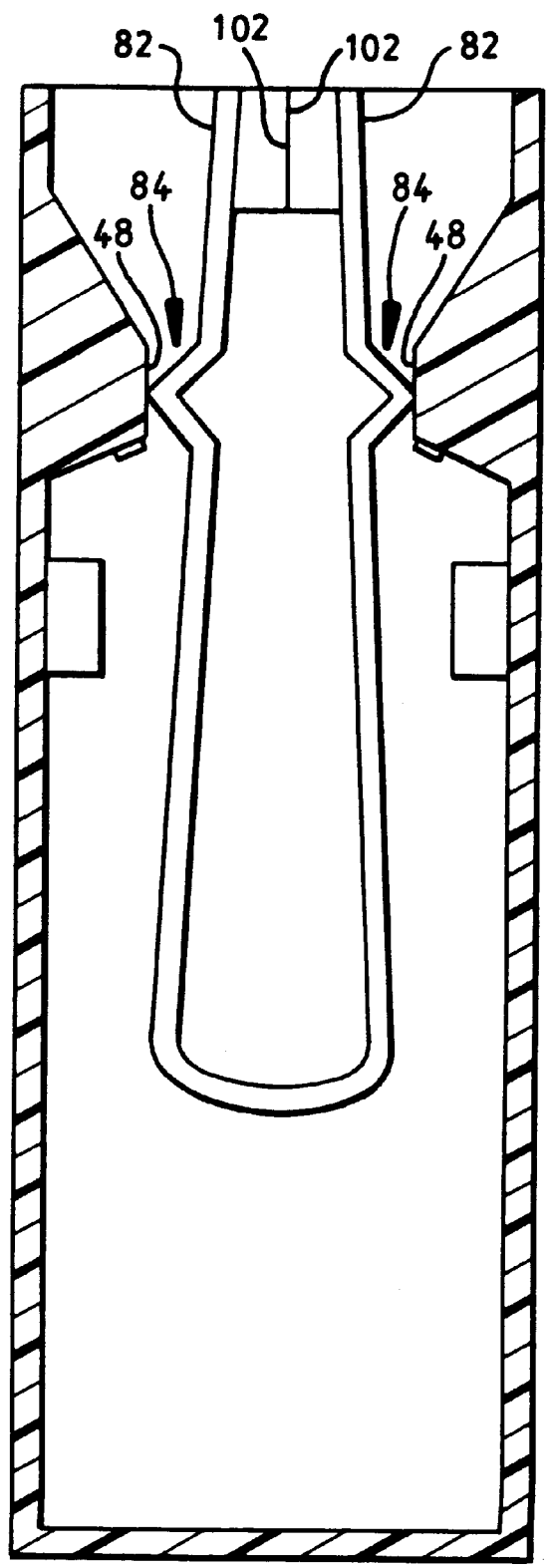
FIG. 10 is a cross-sectional view of the second step of operation.

In FIG. 10, the user has turned the sleeve 26 a short distance. The action of the throat surface 46 on the elbows 84 is a camming mechanism that causes the mating surfaces 102 to make flush contact. This action causes the upper portions of the escapement arms 82 to deform outwardly at the elbows 84. The amount of force holding the mating surfaces 102 and, as a consequence, compressing the saliva sample, is related to the amount of elbow deformation. Preferably, the amount of force between the mating surfaces 102 is approximately 15 grams.

Figure 11:
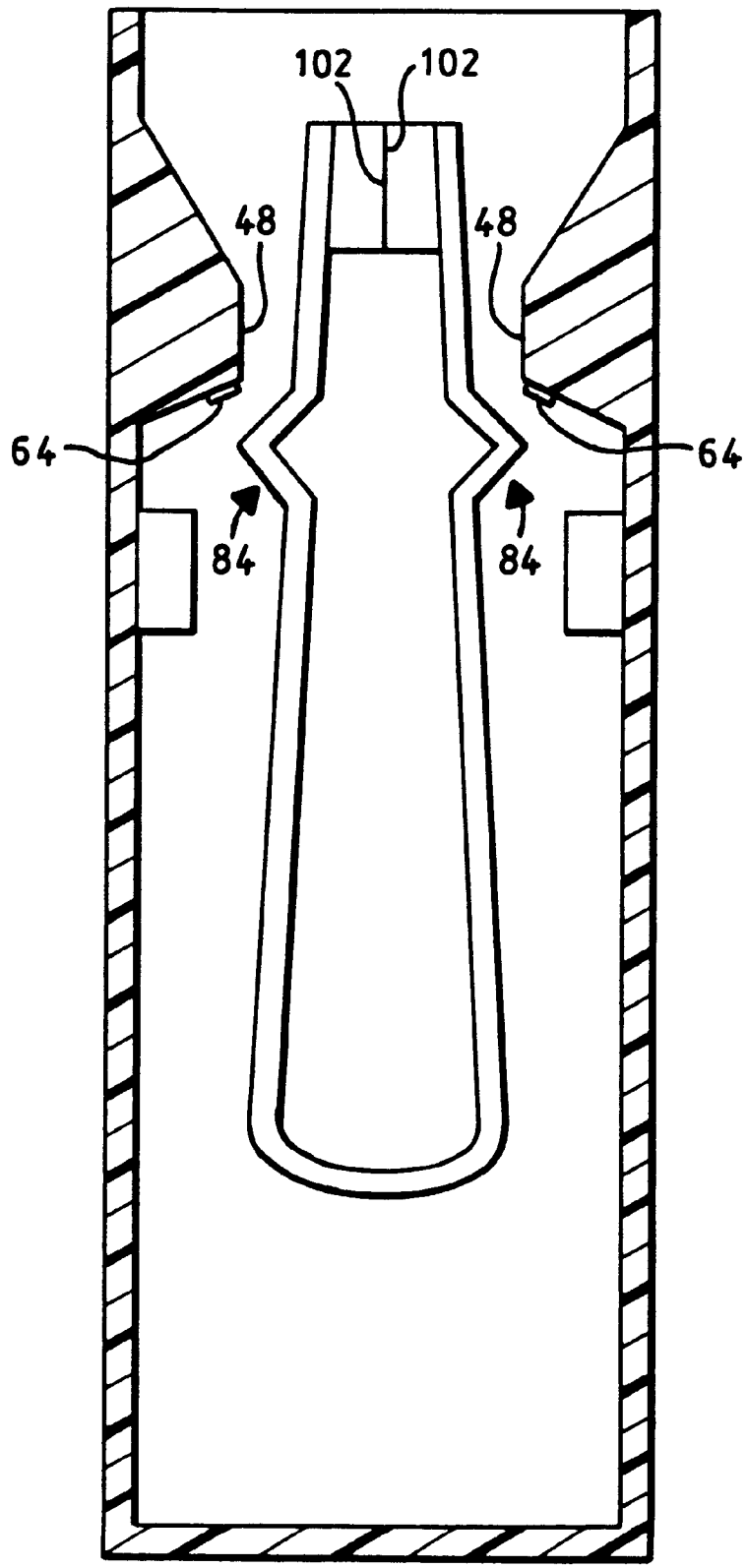
FIG. 11 is a cross-sectional view of the third step of operation.
Figure 12:
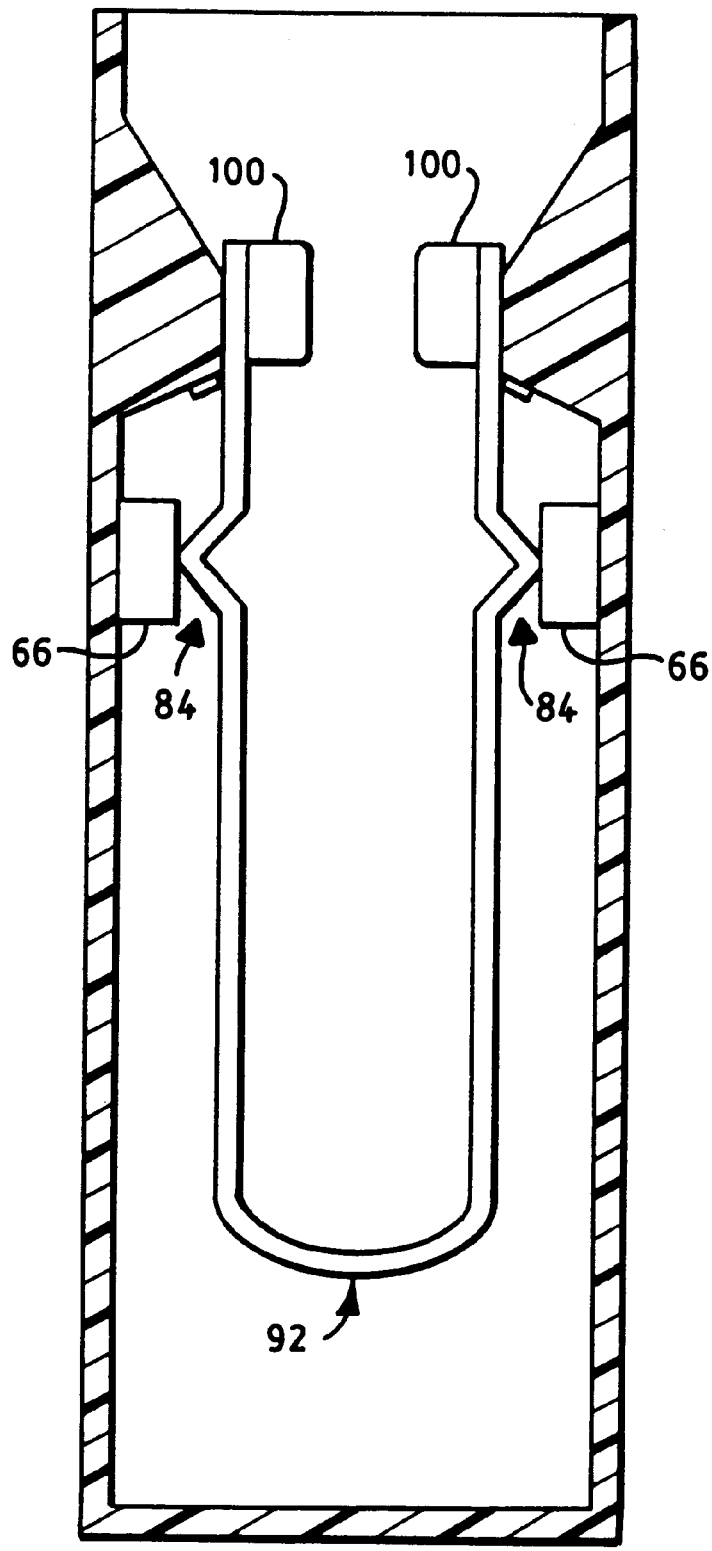
FIG. 12 is a cross-sectional view of the fourth step of operation.

In FIG. 11, the user has continued to turned the sleeve 26. As the elbows 84 pass the bottom of the throat surface 48, they trigger the timer/calculator 62 by electrically connecting the start panels 64. As the escapement 20 continues downward movement, the mating surfaces 102 remain held together by the viscoelasticity of the saliva sample on the mating surfaces 102. In FIG. 12, the escapement 20 has reached the end of its travel. Eventually, the force of the spring 92 overcomes the viscoelasticity of the saliva sample, and the mating surfaces 102 separate. When the mating surfaces 102 separate, the elbows 94 electrically connect the stop panels 66, signaling the timer/calculator 62 to discontinue timing, read the temperature from the temperature sensor 74, adjust the elapsed time, and indicate the result of the measurement on the LED's 70, 72 or LCD.

The Plates

The plates each have a mating surface. The mating surface may be flat or curved. If curved, the surface of one of the plates is convex and the other is concave, with the same radius of curvature. When the mating surfaces are in contact, as described above, the area of contact is substantially the entire surface area of the plates. Preferably, the plates are approximately round with a surface diameter of between 0.5 and 2.0 centimeters (cm), which is a surface area of approximately 0.196 cm$^2$ and 3.14 cm$^2$. The plates are between 0.2 and 0.7 cm thick.

Figure 13:
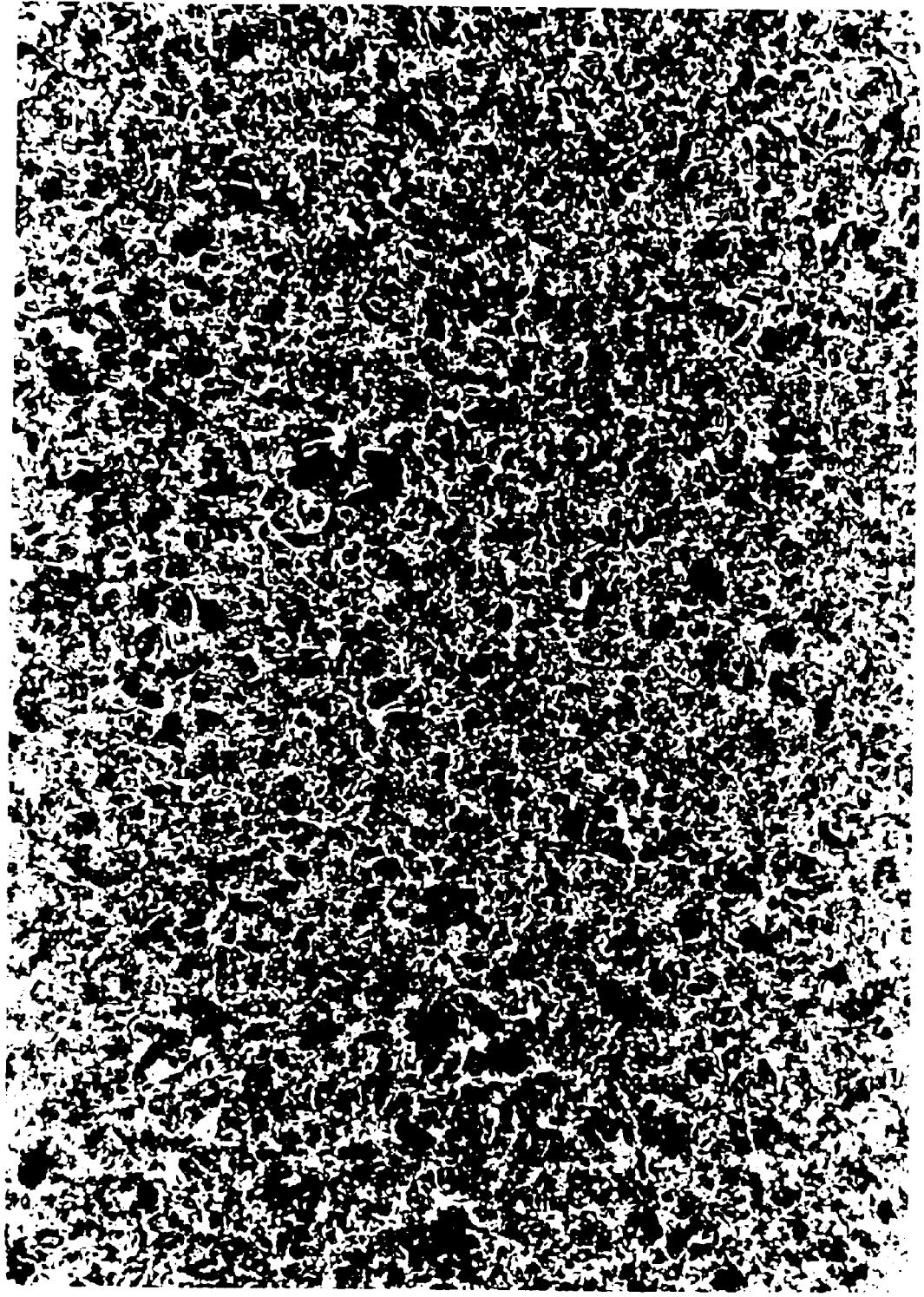
FIG. 13 is a low-power microphotograph of a plate surface.
Figure 14:
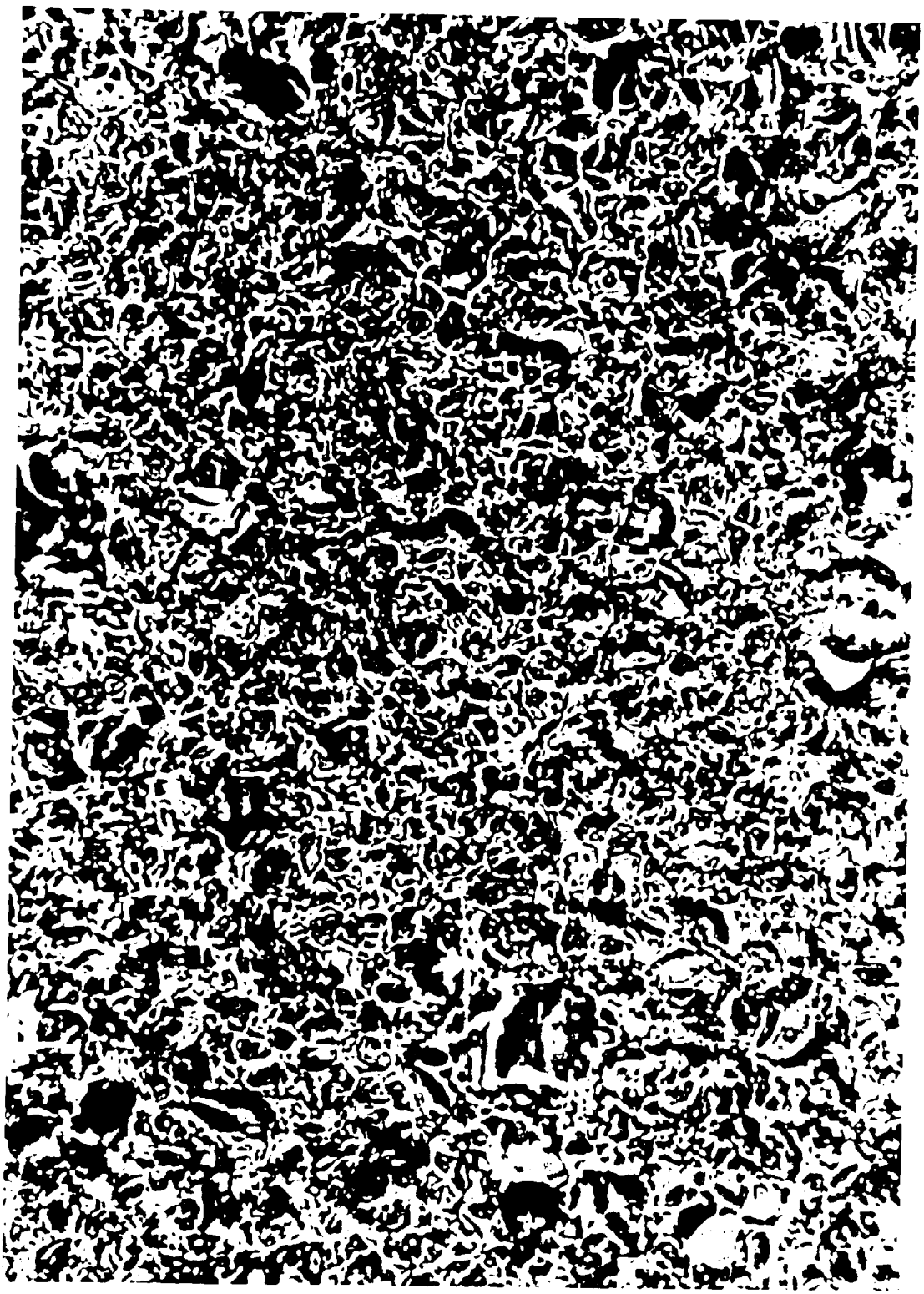
FIG. 14 is a high-power microphotograph of a plate surface.

FIG. 13 is a low-power (10×) microphotograph and FIG. 14 is a high-power (40×) microphotograph of a typical plate surface. As can be seen, the plate surface is rough; it is composed of a random distribution of irregularly shaped valleys and ridges. The height from the floor of a valley to the peak of a ridge is approximately from 0.05 mm to 0.08 mm.

The plates surfaces are roughened so that the saliva sample will fracture internally before it separates from the plate surface. The force of adhesion of the sample to the surfaces must be greater than the force of cohesion of the sample (the amount of force needed to fracture the sample), otherwise the sample will break away from the surface before it fractures, invalidating the measurement.

The plates can be composed of glass or, most preferably, a plastic. In the case of glass, the surface is ground to the above-described roughened surface. In the case of plastic, the surface is etched into a mold from which the plate is formed, eliminating the extra grinding step. Plastic is preferred because the escapement 20 can be molded with the plates as integral components. Additionally, because plastic plates are formed in a mold, there is consistency from one plate to the next.

The plates are intended to be single-use disposable items. The surfaces can be used for one measurement only because the previous saliva sample will dry in the crevices of the surface, causing a subsequent measurement to be invalid since the new saliva sample cannot adhere properly to the surface.

Determination of Fertile Period

The elapsed time measured by the timing circuit 62 is the time it takes for the force of the spring 92 to overcome the tendency of the saliva sample to remain intact, the force of cohesion. The viscoelasticity of the saliva sample is directly related to this time measurement by the following equation:

$$\text{viscosity} = \frac{\text{separation force}/\text{surface area}}{1/\text{separation time}}$$

where the viscosity is calculated in poise (P), the separation force is measured in dynes (dy), the surface area is measured in square centimeters (cm$^2$), and the separation time is measured in seconds (s). The separation force/surface area term is also called the shear stress and the inverse of the separation time is also called the shear rate.

Note that the equation is one for viscosity, rather than for viscoelasticity. When using a Newtonian fluid, such as water, the equation will calculate pure viscosity. However, saliva is a non-Newtonian fluid. In a non-Newtonian fluid, there is an element of elastic recoil, or elasticity, along with the viscosity. Elasticity affects the separation time and separation force of the plates. Thus, the measurements used in the above equation are affected by the elasticity of the saliva sample. Because there is no specific equation for viscoelasticity, the equation for viscosity is used, and the viscoelasticity is measured in viscosity-equivalent units, giving a Newtonian equivalent of the combination of viscosity and elasticity found in the non-Newtonian saliva sample.

The portions of the calculated viscoelasticity attributed to the viscosity and to the elasticity depend upon the thickness of the saliva (density and breadth). As the thickness increases, the portion attributed to viscosity increases as a percentage of the viscoelasticity. For example, in a very thick fluid, the proportion of viscosity to elasticity may be 80% to 20%, while in a very thin fluid, the proportion may be 20% to 80%.

Another factor to consider is that, not only do the proportions of viscosity and elasticity change as a fluid thickens, but the absolute values of the viscosity and elasticity also changes. For example, a thick fluid may have 80% of its viscoelasticity attributed to viscosity and 20% attributed to elasticity with absolute numbers of 64 poise attributed to viscosity and 16 poise attributed to elasticity, and a thin fluid may have 20% of its viscoelasticity attributed to viscosity and 80% attributed to elasticity with absolute numbers of 5 poise attributed to viscosity and 20 poise attributed to elasticity.

The preferred size of the plate surfaces 102 is between about 0.196 cm$^2$ and 3.14 cm$^2$. However, in order for the saliva sample to fracture before it separates from the plate surfaces 102, the plate surfaces 102 are roughened to about twice the nominal surface area, namely from about 0.40 cm$^2$ to about 6.30 cm$^2$. A predetermined constant pressure is applied between the plate surfaces 102 for a minimum period of time of approximately 1 to 4 seconds when the elbows 84 are within the throat 52. This pressure compresses and extrudes the saliva sample between the plate surfaces 102. After the elbows 84 are beyond the throat 52, the pressure of the spring 92 acts to fracture the saliva sample. The spring force is set to about 0.015 dy, giving a shear stress of between about 0.002 dy/cm$^2$ and 0.038 dy/cm$^2$. The shear stress is divided by the inverse of the amount of time measured by the timer 62 to arrive at the viscoelasticity of the saliva sample. For example, if the shear stress is 0.019 dy/cm$^2$ and the separation time is measured as 10 seconds, the viscoelasticity is calculated as 0.19 P or 19 centipoise (cP).

The viscoelasticity of saliva depends, in part, on its temperature; viscoelasticity increases with a decrease in temperature. This means that the separation time decreases as the temperature increases. As a consequence, the separation time must be adjusted to account for the difference in temperature from a baseline temperature. The viscoelasticity calculations above assume a temperature of approximately 20° C. Using 20° C. as a baseline, the separation time must be adjusted upward by approximately 2% for each degree change downward from 20° C. and adjusted downward by approximately 2% for each degree change upward from 20° C. For example, if the separation time is measured at 10 seconds and the temperature is 17° C., the adjusted separation time is 10+((20−17)×0.02×10)=10.6 seconds. If the separation time is measured at 10 seconds and the temperature is 24° C., the adjusted separation time is 10+((20−24)×0.02×10)=9.2 seconds.

Figure 15:
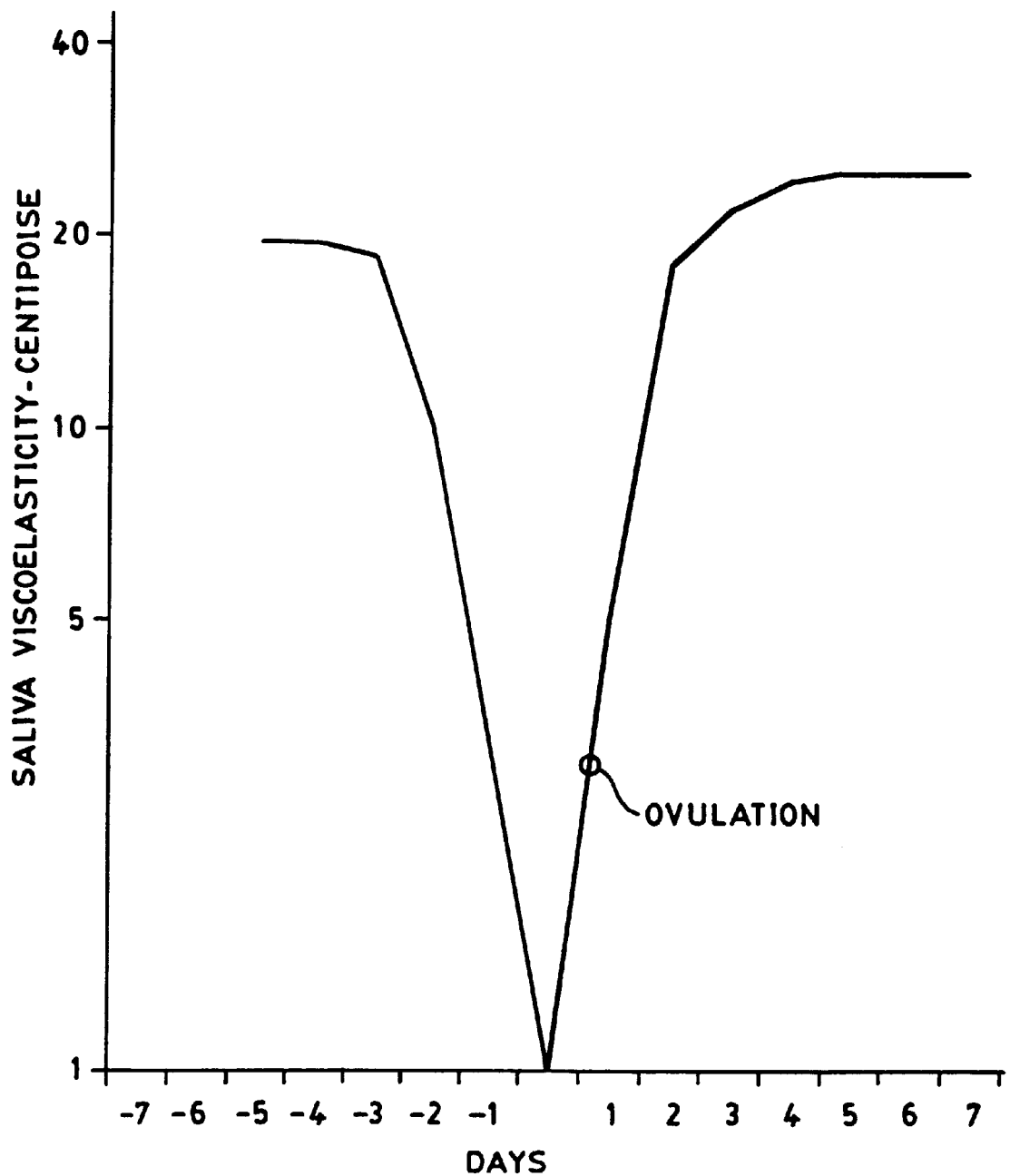
FIG. 15 is a curve showing the relationship between the viscoelasticity of saliva and ovulation time.

There are several different types of saliva, including sublingual and submandibular. The saliva pool under the tongue, the preferred source of saliva for the present invention, is composed in large part of sublingual saliva with some small part of submandibular. The small amount of submandibular saliva in the saliva pool under the tongue does not significantly affect the viscoelasticity of the sublingual saliva. The curve of FIG. 15 shows how the viscoelasticity of sublingual saliva relates to the fertile period. The viscoelasticity falls over a period of from 2 to 4 days until about 16 to 24 hours prior to ovulation and then rises over a period of from 1 to 2 days. Note that a viscoelasticity of 5.1 cP shows that the women is either about 2 days prior to ovulation or immediately after ovulation.

Operation

Figure 7:
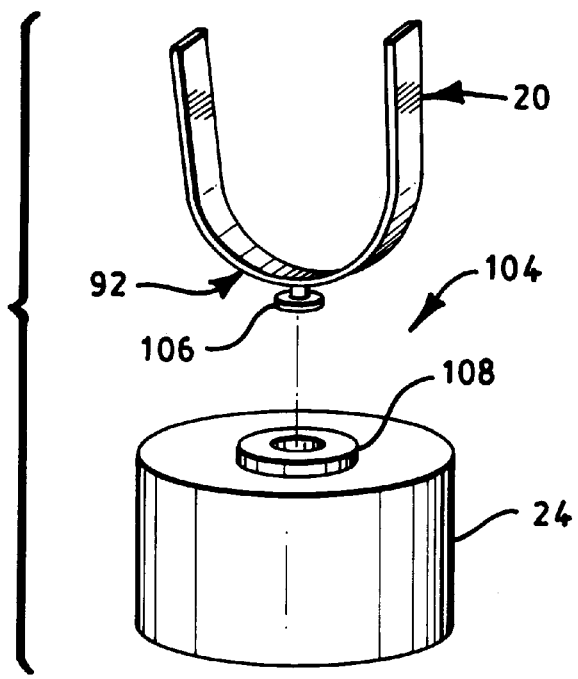
FIG. 7 is a perspective view of one embodiment of the escapement/piston connector.
Figure 8:
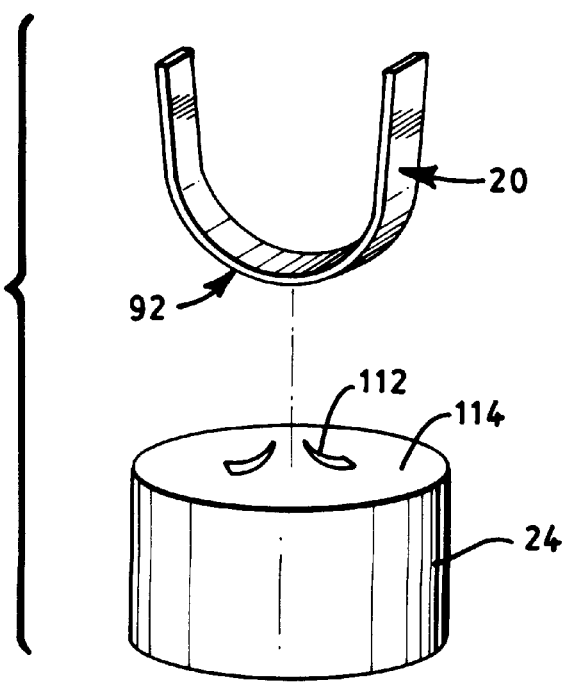
FIG. 8 is a perspective view of another embodiment of the escapement/piston connector.

The instrument 10 is designed so that the escapement 20 is disposable. Prior to usage, a new escapement 20 is acquired and inserted into the sheath 12. If the snap embodiment of FIG. 7 is used, the escapement 20 is pushed into the cavity 40 until the male component 106 snaps into the female component 108. If the tongue embodiment of FIG. 8 is used, the escapement 20 is pushed into the cavity 40 until the tongues 112 snap up over the spring 92 of the escapement 20. During the insertion process, care must be taken to avoid contaminating the plate surfaces 102 with any foreign substance, as such contamination will invalidate the measurement.

After the escapement 20 is in place within the sheath 12, the plates 100 are dipped into the mouth in order to retrieve a sample of saliva from the saliva pool under the tongue. The saliva should cover substantially the entire plate surface 102. After taking the saliva sample, the sleeve 26 is turned its full range in a relatively smooth motion. If a relatively motion is not maintained or the sleeve 26 is not turned its full range, an invalid measurement may result. After a period of time, one of the LED's 70, 72 will illuminate momentarily. If one LED 70 illuminates, it is between approximately 48 hours and 5 hours before ovulation. If the other LED 72 illuminates, it is not within that time period before ovulation.

The escapement 20 is removable for disposal. To remove the escapement 20, the sleeve 26 is turned so that the piston 24 is at its upper limit and the escapement 20 is extending from the sheath 12. The escapement 20 manually pulled hard enough to separate the snap components 106, 108 or to pull the escapement 20 from the tongues 112. The escapement 20 is then manually removed and disposed of.

In alternate embodiment, the entire instrument is disposable. In this embodiment, the instrument is acquired with the escapement already installed. After being used for a single measurement, the instrument is disposed of properly.

Thus it has been shown and described an instrument for measuring saliva viscoelasticity to determine a woman's fertile period which satisfies the objects set forth above.

Since certain changes may be made in the present disclosure without departing from the scope of the present invention, it is intended that all matter described in the foregoing specification and shown in the accompanying drawings be interpreted as illustrative and not in a limiting sense.

What is claimed is:

1. An instrument for determining female fertile period by measuring the viscoelasticity of saliva, said device comprising:
    (a) an elongated sheath having a length along an axis and an opening at one extremity, said sheath including a barrel, a piston that reciprocates axially within said barrel, and a rotating control for moving said piston axially within said barrel;
    (b) an escapement including a pair of elongated arms disposed approximately parallel to said axis, said arms having inner extremities remote from said opening and attached to said piston, and outer extremities in the vicinity of said opening, said outer extremities having mating surfaces;
    (c) said escapement including a spring bias urging separation of said mating surfaces from each other;
    (d) said arms being mounted for relative movement of said mating surfaces among first relational positions at which said mating surfaces are separated, second relational positions at which said mating surfaces are in contact, and third relational positions at which said mating surfaces are free to separate under said spring bias;
    (e) said piston axial motion optionally placing said mating surfaces into said first relational positions, said second relational positions, and said third relational positions;
    (f) a temperature sensor for measuring the approximate temperature of said saliva;
    (g) at least one of said mating surfaces being free to collect said saliva when said mating surfaces are in said first relational positions;
    (h) said mating surfaces being constrained to compress said saliva therebetween when said mating surfaces are in said second relational positions;
    (i) a means for measuring the time elapsed for separation of said surfaces when said mating surfaces are in said third relational positions and for adjusting said elapsed time based on said temperature.

2. The instrument of claim 1 wherein said temperature sensor measures the temperature of said escapement to approximate said temperature of said saliva and uses said escapement temperature in said elapsed time adjustment.

3. The instrument of claim 1 wherein said saliva is a combination of sublingual and mandibular saliva.

4. The instrument of claim 1 wherein said escapement is removable for disposal and replacement.

5. The instrument of claim 1 wherein each of said outer extremities includes a plate, said mating surface being on said plate.

6. The instrument of claim 1 wherein said mating surfaces are adapted to retain said saliva in a manner that causes said saliva to internally fracture before said saliva overcomes its adhesion to said mating surfaces.

7. The instrument of claim 1 wherein said spring bias is produced at a junction at said inner extremities of said arms.

8. The instrument of claim 1 wherein said sheath includes a camming mechanism for moving said mating surfaces from said first relational position into said second relational positions and from said second relational positions to said third relational positions.

9. The instrument of claim 8 wherein said camming mechanism includes opposing elbows on said arms and a throat within said sheath aligned with said axis, whereby the movement of said elbows into said throat causes said mating surfaces to move from said first relational positions to said second relational positions and the movement of said elbows out of said throat causes said mating surfaces to move from said second relational positions to said third relational positions.

10. The instrument of claim 1 wherein said measuring and adjusting means is an electronic circuit.

11. The instrument of claim 1 wherein said instrument includes a visual indicator for indicating the result of said measurement and adjustment.

12. An instrument for determining female fertile period by measuring the viscoelasticity of saliva, said device comprising:
    (a) an elongated sheath having a length along an axis and an opening at one extremity, said sheath including a barrel, a piston that reciprocates axially within said barrel, and a rotating control for moving said piston axially within said barrel;
    (b) an escapement including a pair of elongated arms disposed approximately parallel to said axis, said arms having inner extremities remote from said opening and attached to said piston, and outer extremities in the vicinity of said opening, said outer extremities having mating surfaces that are adapted to retain said saliva in a manner that causes said saliva to internally fracture before said saliva overcomes its adhesion to said mating surfaces;

(c) said escapement including a spring bias urging separation of said mating surfaces from each other;

(d) said arms being mounted for relative movement of said mating surfaces among first relational positions at which said mating surfaces are separated, second relational positions at which said mating surfaces are in contact, and third relational positions at which said mating surfaces are free to separate under said spring bias;

(e) said piston axial motion optionally placing said mating surfaces into said first relational positions, said second relational positions, and said third relational positions;

(f) said sheath including a camming mechanism for moving said mating surfaces from said first relational position into said second relational positions and from said second relational positions to said third relational positions;

(g) a temperature sensor for measuring the temperature of said escapement to approximate the temperature of said saliva;

(h) at least one of said mating surfaces being free to collect said saliva when said mating surfaces are in said first relational positions;

(i) said mating surfaces being constrained to compress said saliva therebetween when said mating surfaces are in said second relational positions;

(j) an electronic circuit for measuring the time elapsed for separation of said surfaces when said mating surfaces are in said third relational positions and for adjusting said elapsed time based on said escapement temperature; and (k) a visual indicator for indicating the result of said measurement and adjustment.

13. The instrument of claim 12 wherein said escapement is removable for disposal and replacement.

14. The instrument of claim 12 wherein each of said outer extremities includes a plate, said mating surface being on said plate.

15. The instrument of claim 12 wherein said spring bias is produced at a junction at said inner extremities of said arms.

16. The instrument of claim 12 wherein said camming mechanism includes opposing elbows on said arms and a throat within said sheath aligned with said axis, whereby movement of said elbows into said throat causes said mating surfaces to move from said first relational positions to said second relational positions and movement of said elbows out of said throat causes said mating surfaces to move from said second relational positions to said third relational positions.

17. An instrument for determining female fertile period by measuring the viscoelasticity of saliva, said device comprising:

(a) an elongated sheath having a length along an axis and an opening at one extremity, said sheath including a barrel, a piston that reciprocates axially within said barrel, and a rotating control for moving said piston axially within said barrel;

(b) an escapement including a pair of elongated arms disposed approximately parallel to said axis, said arms having inner extremities remote from said opening and removably attached to said piston, and outer extremities in the vicinity of said opening, said outer extremities having mating surfaces that are adapted to retain said saliva in a manner that causes said saliva to internally fracture before said saliva overcomes its adhesion to said mating surfaces;

(c) a junction at the inner extremities of said arms producing a spring bias urging separation of said mating surfaces from each other;

(d) said arms being mounted for relative movement of said mating surfaces among first relational positions at which said mating surfaces are separated, second relational positions at which said mating surfaces are in contact, and third relational positions at which said mating surfaces are free to separate under said spring bias;

(e) said piston axial motion optionally placing said mating surfaces into said first relational positions, said second relational positions, and said third relational positions;

(f) said sheath including a camming mechanism for moving said mating surfaces from said first relational position into said second relational positions and from said second relational positions to said third relational positions;

(g) said camming mechanism including opposing elbows on said arms and a throat within said sheath aligned with said axis, whereby movement of said elbows into said throat causes said mating surfaces to move from said first relational positions to said second relational positions and movement of said elbows out of said throat causes said mating surfaces to move from said second relational positions to said third relational positions;

(h) a temperature sensor for measuring the temperature of said escapement to approximate the temperature of said saliva;

(i) at least one of said mating surfaces being free to collect said saliva when said mating surfaces are in said first relational positions;

(j) said mating surfaces being constrained to compress said saliva therebetween when said mating surfaces are in said second relational positions;

(k) an electronic circuit for measuring the time elapsed for separation of said surfaces when said mating surfaces are in said third relational positions and for adjusting said elapsed time based on said escapement temperature; and (l) a visual indicator for indicating the result of said measurement and adjustment.

* * * * *